(12) United States Patent
Honda

(10) Patent No.: US 10,010,363 B2
(45) Date of Patent: Jul. 3, 2018

(54) ENERGY TREATMENT INSTRUMENT

(71) Applicant: OLYMPUS CORPORATION, Hachioji-shi, Tokyo (JP)

(72) Inventor: Yoshitaka Honda, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/602,257

(22) Filed: May 23, 2017

(65) Prior Publication Data
US 2017/0252088 A1 Sep. 7, 2017

Related U.S. Application Data

(63) Continuation of application No. PCT/JP2016/066931, filed on Jun. 7, 2016.

(30) Foreign Application Priority Data

Jun. 17, 2015 (JP) ................. 2015-121626

(51) Int. Cl.
| | | |
|---|---|---|
| *A61B 18/12* | (2006.01) | |
| *A61B 18/10* | (2006.01) | |
| *A61B 18/14* | (2006.01) | |
| *A61N 7/02* | (2006.01) | |

(Continued)

(52) U.S. Cl.
CPC .......... *A61B 18/10* (2013.01); *A61B 18/1206* (2013.01); *A61B 18/1445* (2013.01); *A61N 7/02* (2013.01); *A61B 2017/00402* (2013.01); *A61B 2017/00407* (2013.01); *A61B 2018/0019* (2013.01); *A61B 2018/00202* (2013.01);
(Continued)

(58) Field of Classification Search
CPC . A61B 18/10; A61B 18/1206; A61B 18/1445; A61B 2017/00402; A61B 2017/00407; A61B 2018/0019; A61B 2018/00202; A61B 2018/00952; A61B 2018/00994; A61N 7/02
USPC ....................... 290/1 C; 310/47, 50
See application file for complete search history.

(56) References Cited

U.S. PATENT DOCUMENTS

| | | | | |
|---|---|---|---|---|
| 2009/0033100 A1* | 2/2009 | Dai | ...................... | H02K 7/1853 290/1 C |
| 2011/0224663 A1* | 9/2011 | Heim | .................. | A61B 18/1206 606/33 |

FOREIGN PATENT DOCUMENTS

| | | |
|---|---|---|
| JP | H10-290783 A | 11/1998 |
| JP | 2000-287986 A | 10/2000 |
| JP | 2006-068537 A | 3/2006 |

(Continued)

OTHER PUBLICATIONS

Sep. 6, 2016 International Search Report issued with International Patent Application No. PCT/JP2016/066931.

(Continued)

*Primary Examiner* — Daniel Fowler
(74) *Attorney, Agent, or Firm* — Oliff PLC

(57) ABSTRACT

The energy treatment instrument includes an end effector performing treatment using treatment energy, and a moving part disposed so as to be movable relative to a housing and moving relative to the housing based on an operation input to move the end effector or an operation input to supply treatment energy to the end effector. The energy treatment instrument includes an energy converter converting kinetic energy due to a movement of the moving part into electric energy and storing the converted electric energy in an electricity storage.

9 Claims, 3 Drawing Sheets

(51) Int. Cl.
*A61B 17/00* (2006.01)
*A61B 18/00* (2006.01)

(52) U.S. Cl.
CPC ............... *A61B 2018/00952* (2013.01); *A61B 2018/00994* (2013.01)

(56) References Cited

FOREIGN PATENT DOCUMENTS

| JP | 2006-280958 A | 10/2006 |
| JP | 2010-517681 A | 5/2010 |

OTHER PUBLICATIONS

Dec. 28, 2017 International Preliminary Search Report issued in International Patent Application No. PCT/JP2016/066931.

\* cited by examiner

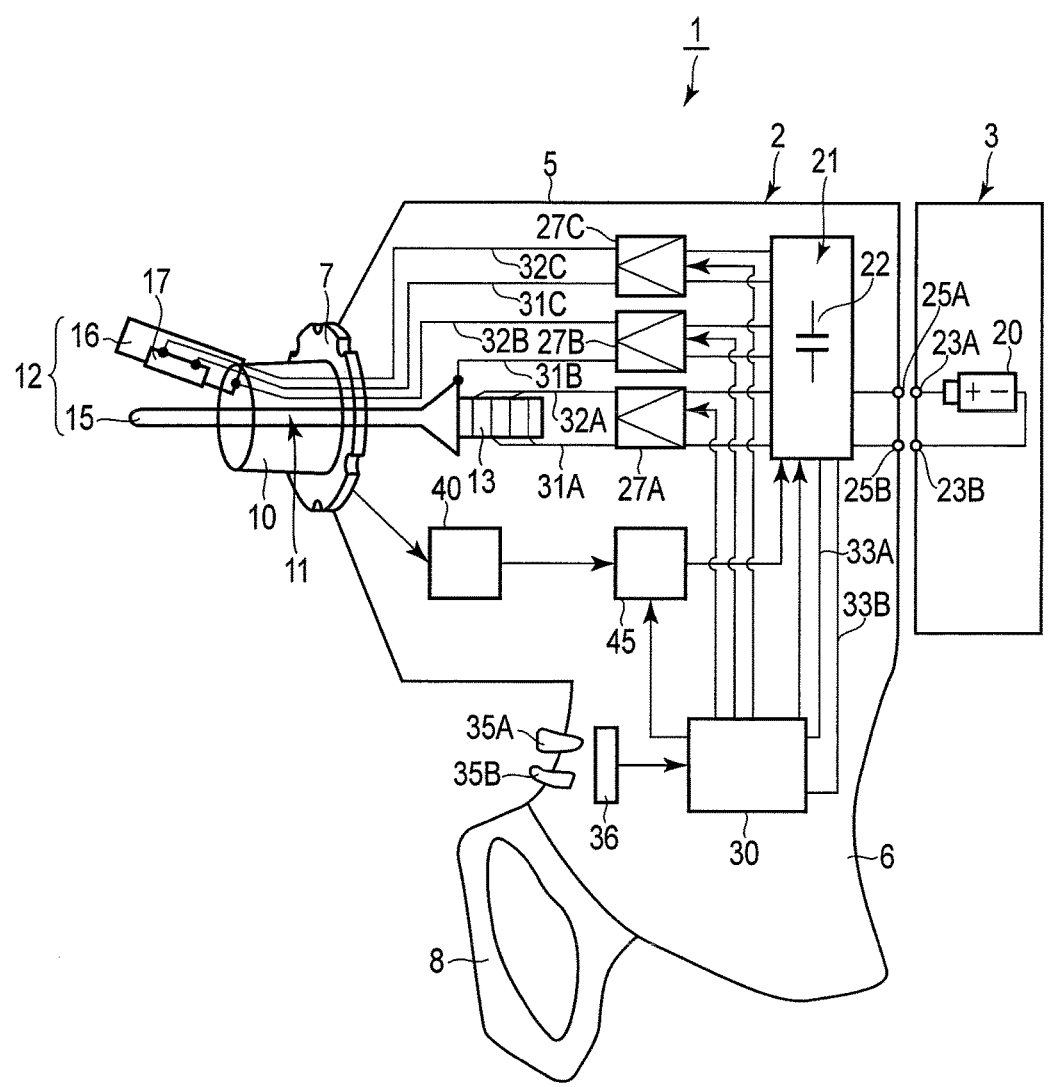
F I G. 1

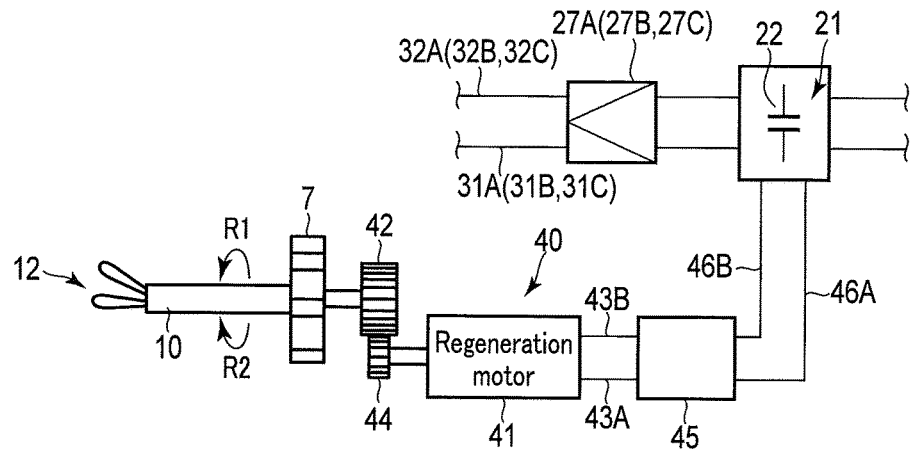
F I G. 2
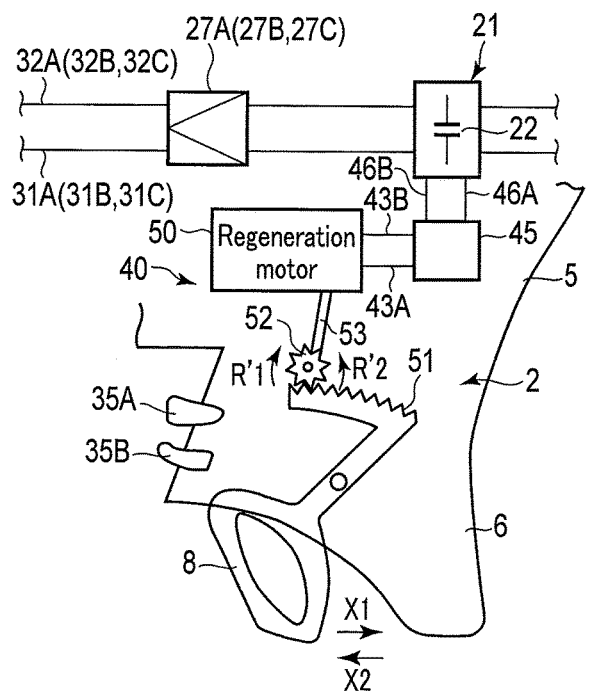
F I G. 3

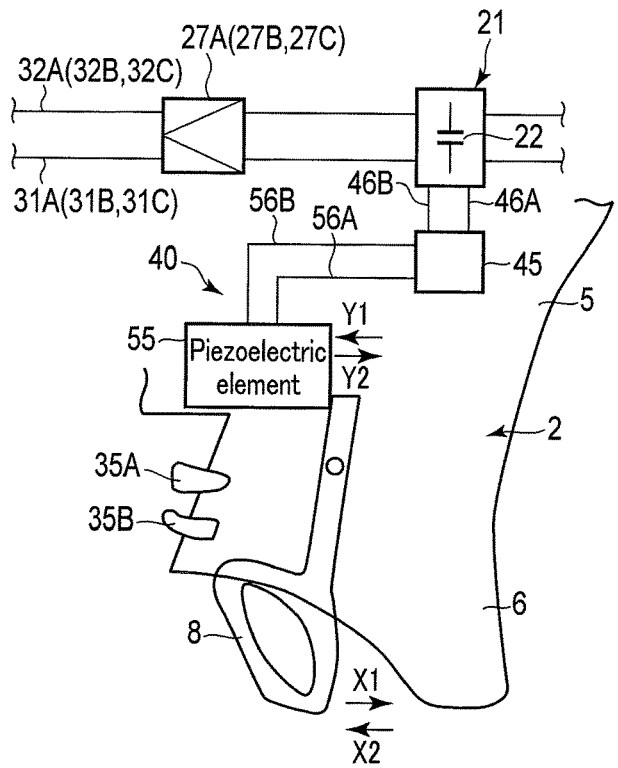
F I G. 4
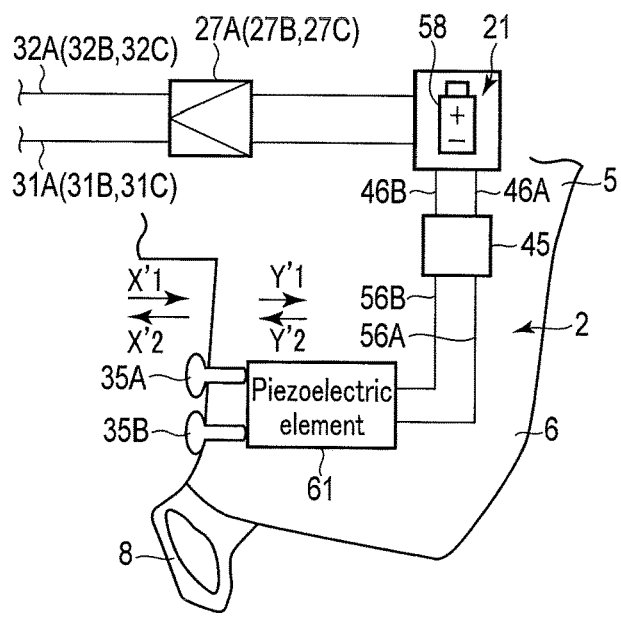
F I G. 5

ENERGY TREATMENT INSTRUMENT

CROSS-REFERENCE TO RELATED APPLICATIONS

This is a Continuation Application of PCT Application No. PCT/JP2016/066931, filed Jun. 7, 2016 and based upon and claiming the benefit of priority from prior Japanese Patent Application No. 2015-121626, filed Jun. 17, 2015, the entire contents of which are incorporated herein by reference.

BACKGROUND OF THE INVENTION

1. Field of the Invention

The present invention relates to an energy treatment instrument that generates treatment energy from electric energy so as to perform treatment using the generated treatment energy.

2. Description of the Related Art

Jpn. Pat. Appln. KOKAI Publication No. 2006-68537 discloses an energy treatment instrument in which electric energy from a battery is converted into electric energy that generates ultrasonic vibration in a driving circuit that is a treatment energy generator, and the electric energy converted in the driving circuit is supplied to an ultrasonic transducer to thereby generate ultrasonic vibration. In this energy treatment instrument, ultrasonic vibration generated in the ultrasonic transducer is transmitted as treatment energy to an end effector, and the end effector performs treatment using the ultrasonic vibration. Furthermore, in the energy treatment instrument, an electric power generator to convert a rotational movement of a rotary handle into electric energy is provided, and the electric energy generated in the electric power generator is stored in a battery.

BRIEF SUMMARY OF THE INVENTION

According to one aspect of the invention, an energy treatment instrument including: a retainable housing; an electricity storage capable of storing electric energy; an end effector configured to perform treatment using treatment energy; a moving part which is disposed so as to be movable relative to the housing, and which is configured to move relative to the housing based on an operation input to move the end effector or an operation input to supply the treatment energy to the end effector; and an energy converter configured to convert kinetic energy brought by a movement of the moving part into electric energy, and configured to store the converted electric energy in the electricity storage.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram showing an energy treatment instrument according to a first embodiment, FIG. 2 is a schematic diagram explaining the configuration of an energy converter and an electric power converter, according to the first embodiment, FIG. 3 is a schematic diagram explaining an energy converter and an electric power converter according to one modification of the first embodiment, FIG. 4 is a schematic diagram explaining the configuration of an energy converter and an electric power converter, according to a second embodiment, and FIG. 5 is a schematic diagram explaining the configuration of an energy converter and an electric power converter according to one modification of the second embodiment.

DETAILED DESCRIPTION OF THE INVENTION

First Embodiment

A first embodiment of the present application will be explained in reference to FIGS. 1 and 2. FIG. 1 is a diagram showing an energy treatment instrument 1 used mainly cordlessly. As shown in FIG. 1, the energy treatment instrument 1 includes a retainable housing 2, and a battery unit 3 detachably attached to the housing 2. In the present embodiment, the housing 2 includes a housing body 5, and a grip (fixed handle) 6 extending from the housing body 5 toward a direction that intersects with a central axis of the housing body 5. Herein, in the energy treatment instrument 1, one side of a direction parallel to the central axis of the housing body 5 is regarded as a distal direction (distal side), and the opposite side to the distal direction is regarded as a proximal direction (proximal side).

On the distal side of the housing body 5, a rotation knob 7 is mounted substantially coaxially with the housing body 5. The rotation knob 7 is rotatable around the central axis (axis) relative to the housing 2. Also, a handle (movable handle) 8 is attached to the housing 2 so as to be openable and closable relative to the grip 6.

A sheath 10 is coupled to the housing 2 in a state where the sheath is inserted into the inside of the rotation knob 7 and the inside of the housing body 5 from the distal side. The sheath 10 is provided substantially coaxially with the housing body 5. Furthermore, in the energy treatment instrument 1, a vibration transmitter (rod portion) 11 capable of transmitting ultrasonic vibration extends from the inside of the housing body 5 through the inside of the sheath 10 toward the distal side. To the proximal portion of the vibration transmitter 11, a ultrasonic transducer 13, which includes a piezoelectric element converting electric energy (alternating-current electric power) into ultrasonic vibration, is attached. In addition, the vibration transmitter 11 includes a first grasping piece (rod treatment portion) 15 projecting from the distal end of the sheath 10 toward the distal side. A second grasping piece (jaw) 16 is attached pivotally to the distal portion of the sheath 10. By allowing the second grasping piece 16 to pivot, the first grasping piece 15 and the second grasping piece 16 are opened or closed relative to each other. That is, the first grasping piece 15 the second grasping piece 16 can open and close relative to each other. Note that the vibration transmitter 11 is formed of a conductive material.

In the present embodiment, an end effector 12 that treats a treated target such as a living tissue by using supplied treatment energy is formed by the first grasping piece 15 and the second grasping piece 16. In the present embodiment, during treatment, the treated target is grasped between the first grasping piece 15 and the second grasping piece 16 to give the supplied treatment energy to the grasped treated target. Furthermore, in the present embodiment, a heater (heat generator) 17, which converts electric energy (direct-current electric power or alternating-current electric power) into heat energy is provided in the second grasping piece 16.

By rotationally moving the rotation knob 7 around the central axis, the sheath 10, vibration transmitter 11 (first grasping piece 15), ultrasonic transducer 13, and second grasping piece 16 rotate around the central axis of the rotation knob 7 relative to the housing 2. That is, in the rotation knob 7, an operation to rotate the end effector 12 around the central axis of the rotation knob 7 is input. Additionally, by moving the handle 8 to open or close relative to the grip 6 of the housing 2 by means of an advance or retreat movement, a movable pipe (not shown) of the sheath 10 moves along the central axis of the sheath 10. With this configuration, the second grasping piece 16 pivots relative to the sheath 10, and the first grasping piece 15 and the second grasping piece 16 open or close relative to each other. That is, in the handle 8, an operation to open or close between the first grasping piece 15 and the second grasping piece 16 is input.

The battery unit 3 includes a battery 20. Also, an electricity storage 21 capable of storing electric energy is disposed inside the housing 2. The electricity storage 21 includes a charge tank 22 which is, for example, a capacitor. The battery unit 3 is installed on the housing 2, thereby an electric contact 23A comes into contact with an electric contact 25A, and an electric contact 23B comes into contact with an electric contact 25B. With this configuration, the battery 20 is electrically connected to the electricity storage 21. Note that a plurality of batteries 20 may be arranged in the battery unit 3. In this case, all the batteries 20 are electrically connected to the electricity storage 21 by attaching the battery unit 3 to the housing 2.

Inside the housing 2, a first amplifier circuit (ultrasonic driving circuit) 27A, a second amplifier circuit (high-frequency driving circuit) 27B and a third amplifier circuit (heat driving circuit) 27C are arranged as a treatment energy generator that generates treatment energy to be supplied to the end effector 12. The first amplifier circuit 27A is electrically connected to the ultrasonic transducer 13 via electric paths 31A and 32A. Furthermore, the second amplifier circuit 27B is electrically connected to the vibration transmitter 11 via an electric path 31B and is electrically connected to the second grasping piece 16 via an electric path 32B. And the third amplifier circuit 27C is electrically connected to the heater 17 via electric paths 31C and 32C.

A controller 30 is disposed inside the housing 2. The controller 30 includes a processor which includes a CPU (Central Processing Unit) or ASIC (application specific integrated circuit); a clock signal generating circuit; and a storage medium such as a memory. Electric energy is supplied to the controller 30, by which the clock signal generating circuit generates a clock signal, and the controller is brought into actuating by the generated clock signal. The controller 30 is electrically connected to the electricity storage 21 via electric paths 33A and 33B. Also, the controller 30 controls supply of electric energy from the electricity storage 21 and controls driving of the amplifier circuits 27A to 27C.

Operation buttons 35A and 35B are attached to the grip 6 of the housing 2. At each of the operation buttons 35A and 35B, an operation input is performed by pressing down each of the operation buttons, and each of the operation buttons 35A and 35B performs an advance or retreat movement by the operation input. Inside the housing 2, a detecting circuit 36 is provided to detect whether the operation input is performed at each of the operation buttons 35A, 35B. In the detecting circuit 36, switches (not shown) each of which is corresponding to, for example, one of the operation buttons 35A and 35B, are provided, and each of the switches switches between an opened state and a closed state based on an operation input at the corresponding operation button (corresponding one of 35A and 35B). The controller 30 controls the electricity storage 21 and amplifier circuits 27A to 27C based on the detected result in the detecting circuit 36.

For example, upon detection of an operation input at the operation button 35A, the controller 30 controls the electricity storage 21 and amplifier circuits 27A to 27C, thereby the first amplifier circuit 27A converts electric energy (direct-current electric power) supplied from the electricity storage 21 into electric energy (alternating-current electric power) that generates ultrasonic vibration. The vibration generation electric energy (alternating-current electric power) generated as treatment energy in the first amplifier circuit 27A is supplied to the ultrasonic transducer 13 via the electric paths 31A and 32A, and ultrasonic vibration is generated in the ultrasonic transducer 13. Then, ultrasonic vibration is transmitted as treatment energy from the ultrasonic transducer 13 to the first grasping piece 15 of the end effector 12 through the vibration transmitter 11.

Upon detection of an operation input at the operation button 35A, the controller 30 controls the electricity storage 21 and amplifier circuits 27A to 27C, thereby the second amplifier circuit 27B converts electric energy (direct-current electric power) supplied from the electricity storage 21 into high-frequency electric energy (alternating-current electric power). Thus, the high-frequency electric energy generated as treatment energy at the second amplifier circuit 27B is supplied to the first grasping piece 15 of the end effector 12 via the electric path 31B and vibration transmitter 11, and is also supplied to the second grasping piece 16 of the end effector 12 via the electric path 32B. The high-frequency energy is supplied as treatment energy to the first grasping piece 15 and the second grasping piece 16, thereby the first grasping piece 15 and second grasping piece 16 function as electrodes of high-frequency electric energy having a different electric potential from each other.

For example, upon detection of an operation input at the operation button 35B, the controller 30 controls the electricity storage 21 and amplifier circuits 27A to 27C, thereby the third amplifier circuit 27C converts electric energy (direct-current electric power) supplied from the electricity storage 21 into electric energy (direct-current electric power or alternating-current electric power) that generates heat. Thus, the heat generating electric energy (direct-current electric power or alternating-current electric power) generated as treatment energy in the third amplifier circuit 27C is supplied to the heater 17 via electric paths 31C and 32C, and heat is generated in the heater 17. The heat generated in the heater 17 is conveyed as treatment energy to the second grasping piece of the end effector 12.

As described above, at each of the operation buttons 35A and 35B, an operation input to supply treatment energy to the end effector 12 is input. Note that in the present embodiment, as treatment energy to be supplied to the end effector 12, ultrasonic vibration (vibration generating electric energy), high-frequency electric energy, and heat (heat generating electric energy) can be generated, however, one or two of the ultrasonic vibration, high-frequency electric energy and heat may be generated as treatment energy. In addition, energy different from ultrasonic vibration, high-frequency electric energy and heat may be generated as treatment energy and supplied to the end effector 12.

Inside the housing 2, an energy converter 40 and an electric power converter 45 are arranged. FIG. 2 is a schematic diagram explaining the configuration of the energy converter 40 and the electric power converter 45. As shown in FIG. 2, the energy converter 40 includes a regeneration motor 41 that functions as an electric power generator generating electric power by conveying motive power (kinetic energy) thereto. The regeneration motor 41 is coupled to the rotation knob 7 through a gear 42 and a gear 44. The gear 42 is provided coaxially with the rotation knob 7, the gear 44 is provided coaxially with the regeneration motor 41, and the gear 42 is engaged with the gear 44. The rotation knob 7 rotationally moves around the central axis based on an operation input to rotate the end effector 12 around the central axis of the rotation knob 7, by which the motive power is conveyed to the regeneration motor 41 through the gears 42 and 44. That is, based on the operation input to move the end effector 12, the rotation knob 7 that is a moving part moves relative to the housing 2, and by the movement of the rotation knob 7 relative to the housing 2, the motive power (kinetic energy) is conveyed to the regeneration motor 41.

Through transmission of the motive power to the regeneration motor 41, electric power is generated at the regeneration motor 41. With this configuration, the rotational movement around the central axis of the rotation knob 7 is converted into electric energy. That is, the energy converter 40 converts kinetic energy due to the movement of the rotation knob 7, which is a moving part, relative to the housing 2, into electric energy.

The regeneration motor 41 is electrically connected to the electric power converter 45 via electric paths 43A, 43B. In the energy converter 40 (regeneration motor 41), kinetic energy is converted into electric energy, thereby generating alternating current electric power. That is, when the rotation knob 7 rotationally moves in one side of a direction around the central axis (a direction indicated by arrow R1 in FIG. 2), electric current flows from the regeneration motor 41 toward the electric path 43A. On the other hand, when the rotation knob 7 rotationally moves in the other side of the direction around the central axis (the direction indicated by arrow R2 in FIG. 2), electric current flows from the regeneration motor 41 toward the electric path 43B, and the direction of the electric current from the regeneration motor 41 is opposite to the direction in the case where the rotation knob 7 rotationally moves toward the one side of the direction around the central axis.

The electric power converter 45 is an electric power converting circuit including a diode and a DC/DC converter, and the driving of the converter is controlled by the controller 30. The electric power converter 45 is electrically connected to the electricity storage 21 via electric paths 46A and 46B. By control of the controller, the electric power converter 45 rectifies alternating-current electric power generated at the energy converter 40 to direct current electric power, and converts the voltage into a voltage in a size that is storable in the electricity storage 21. That is, the electric converter 45 converts alternating-current electric power generated at the energy converter 40 into direct-current electric power having a voltage storable in the electricity storage 21 (charge tank 22).

Therefore, electric energy (direct-current electric power) is supplied from the electric power converter 45 to the electricity storage 21 via electric paths 46A and 46B, and the electric energy (direct-current electric power) is stored in the electricity storage 21 (charge tank 22). That is, kinetic energy is converted into electric energy at the energy converter 40, and the converted electric energy is stored in the electricity storage 21.

The electric energy (direct-current electric power) supplied from the energy converter 40 to the electricity storage 21 may be supplied to any of the amplifier circuits 27A to 27C, and as described above, treatment energy (ultrasonic vibration (vibration generating electric energy), high-frequency electric energy, and heat (heat-generating electric energy)] may be generated, or may be supplied to the battery 20 and stored in the battery 20. Also, the electric energy supplied from the energy converter 40 to the electricity storage 21 may be supplied to the clock signal generating circuit in the controller 30 through electric paths 33A and 33B to actuate (start) the controller 30. The energy treatment instrument 1 may be further provided with an indicator (not shown) such as an LED and a buzzer indicating that treatment energy is supplied to the end effector 12 or that the energy treatment instrument is in a state of risk, so that the electric energy supplied from the energy converter 40 to the electricity storage 21 is supplied to the indicator to actuate the indicator.

Next, function and effects of the energy treatment instrument 1 according to the present embodiment will be explained. When treatment is performed using the energy treatment instrument 1, the battery unit 3 is attached to the housing 2, and the battery 20 is electrically connected to the electricity storage 21. The distal portion of the sheath 10 and the end effector 12 are inserted into a body cavity such as an abdominal cavity. Then, an angular position of the end effector 12 (second grasping piece 16) around the central axis of the rotation knob 7 is adjusted by rotating the rotation knob 7 around the central axis. When the angular position of the end effector 12 around the central axis of the rotation knob 7 is adjusted, the handle is closed relative to the grip 6 so as to grasp a treated target between the first grasping piece 15 and the second grasping piece 16. An operation input is performed at the operation button 35A or 35B in a state where the treated target is grasped between the first grasping piece 15 and the second grasping piece 16, thereby as described above, treatment energy (at least one of ultrasonic vibration, high-frequency electric energy, and heat) is supplied to the end effector 12, and the treated target is treated using the supplied treatment energy.

Supplied with electric energy, each of the amplifier circuits (driving circuits) 27A to 27C converts the electric energy (direct-current electric power) into treatment energy (corresponding one of vibration generating electric energy, high-frequency electric energy and heat generating electric energy) so as to generate treatment energy. In the present embodiment, electric energy (direct-current electric power) from the battery 20 is stored in the electricity storage 21 and supplied to the amplifier circuits 27A to 27C. Furthermore, by the rotational movement of the rotation knob 7 based on the operation input to rotate the end effector 12, electric energy is generated in the energy converter 40 (regeneration motor 41). The electric energy converted from kinetic energy in the energy converter 40 is stored in the electricity storage 21 (charge tank 22) and is supplied to the amplifier circuits 27A to 27C.

As described above, in the present embodiment, the movement of the rotation knob (moving part) 7 relative to the housing 2, i.e., the rotational movement (kinetic energy) of the rotation knob 7 is converted into electric energy by the energy converter 40, and in addition to the electric energy from the battery 20, the electric energy converted from the kinetic energy in the energy converter 40 is supplied to the amplifier circuits 27A to 27C. In each of the amplifier circuits 27A to 27C, treatment energy is therefore generated using the electric energy from the battery 20 and the electric energy converted from kinetic energy in the energy converter 40. Therefore, even if electric energy to be supplied from the battery 20 to the amplifier circuits 27A to 27C runs short due to a capacity shortage of the battery 20 or the like, each of the amplifier circuits 27A to 27C is capable of generating treatment energy by using electric energy converted from kinetic energy in the energy converter 40. That is, in the present embodiment, electric energy converted from kinetic energy in the energy converter 40 is supplied to the amplifier circuits 27A to 27C, and thus electric energy can be supplied to the amplifier circuits 27A to 27C for long periods and multiple times during treatment. With this configuration, treatment energy can be generated in each of the amplifier circuits 27A to 27C for long periods and multiple times, and thus treatment energy can be supplied to the end effector 12 for long periods and multiple times. Treatment energy is supplied to the end effector 12 for long periods and multiple times, thereby a treated target can be treated stably.

An operation input in the rotation knob 7 to rotate the end effector 12 is necessarily (usually) performed in treatment, and the rotation knob 7 moves rotationally by the operation input necessarily performed in treatment. That is, the rotation knob 7 rotationally moves (motions) relative to the housing 2 by the operation input to move the end effector 12, which is necessarily performed in treatment. Therefore, the surgeon does not need to perform, in treatment, an operation only for generating electric energy from kinetic energy, except for the operation input to move the end effector 12 (an operation input in the rotation knob 17 and an operation input in the handle 8), and the operation input to supply treatment energy to the end effector 12 (an operation input in the operation buttons 35A, 35B). That is, by just only performing the operation input to move the end effector 12, kinetic energy is converted into electric energy in the energy converter 40. For this reason, labor of the operator during treatment are reduced.

Further, the operation input in the rotation knob 7 to rotate the end effector 12 is frequently performed during treatment, and thus in the energy converter 40 (regeneration motor 41), the rotational movement (kinetic energy) of the rotation knob 7 is frequently converted into electric energy. For this reason, electric energy can be supplied to the amplifier circuits 27A to 27C for even longer periods and multiple times during treatment.

The electric energy (alternating-current electric power) generated from kinetic energy in the energy converter 40 is converted into direct-current electric power (electric energy) having a voltage that is storable in the electricity storage 21 by the electric power converter 45. That is, the alternating-current electric power generated at the energy converter 40 is converted, by the electric power converter 45, into direct-current electric power having the same voltage as that of the electric energy (direct-current electric power) supplied from the battery 20 to each of the amplifier circuits 27A to 27C. With this configuration, even if alternating-current electric power is generated by conversion from kinetic energy to electric energy at the energy converter 40, the alternating-current electric power can be supplied to each of the amplifier circuits 27A to 27C after the alternating-current electric power has been properly rectified and the voltage has been properly converted.

In the present embodiment, electric energy to be converted into treatment energy can be supplied, in the manner described above, to each of the amplifier circuits 27A to 27C for long periods and multiple times during treatment, without increasing labor of the operator.

Modifications of First Embodiment

Note that in one modification of the first embodiment shown in FIG. 3, a ratchet 51 is formed in the handle 8. The ratchet 51 is formed in a portion of the handle 8 inserted into the inside of a housing 2. Inside the housing 2, a gear 52 is provided in a state of being engaged with the ratchet 51. By moving the handle 8 to open or close relative to the grip 6 of the housing 2, the motive power from the handle 8 is conveyed to the gear 52, and the gear 52 moves rotationally. That is, based on an operation input to open or close between a first grasping piece 15 and a second grasping piece 16 (an operation input to move the end effector 12), the gear 52 which is a moving part moves (rotationally moves) relative to the housing 2. In the present modification, by closing the handle 8 relative to the grip 6 (arrow X1 in FIG. 3), the gear 52 rotates toward one side (direction of arrow R' in FIG. 3) in the rotational direction. And by opening the handle 8 relative to the grip 6 (arrow X2 in FIG. 3), the gear 52 rotates toward the other side (direction of arrow R'2 in FIG. 3) in the rotational direction.

In the present modification, an energy converter 40 includes a regeneration motor 50, and the regeneration motor 50 is coupled to the gear 52 via a shaft 53. By the rotational movement of the gear 52, motive power is conveyed to the regeneration motor 50, and electric power is generated in the regeneration motor 50. With this configuration, the rotational movement of the gear 52 is converted into electric energy. That is, the energy converter 40 converts kinetic energy due to the movement relative to the housing 2 of the gear 52, which is a moving part, into electric energy.

Also in the present modification, kinetic energy is converted into electric energy in the energy converter 40 (regeneration motor 50), thereby alternating-current electric power is generated. That is, when the gear 52 rotates toward one side in the rotational direction (direction of arrow R'1 in FIG. 3), electric current flows from the regeneration motor 50 toward an electric path 43A. On the other hand, when the gear 52 rotates toward the other side in the rotational direction (direction of arrow R'2 in FIG. 3), electric current flows from the regeneration motor 50 to an electric path 43B, and the direction of the electric current from the regeneration motor 50 is opposite to the direction in the case where the gear 52 rotates toward the one side of the rotational direction.

In the present modification as well, the electric energy converted in the energy converter 40 is converted from alternating-current electric power to direct-current electric power having a voltage storable in the electricity storage 21 by the electric power converter 45. Further, the electric energy from the energy converter 40 is stored in the electricity storage 21 (charge tank 22), and is supplied to each of the amplifier circuits 27A to 27C or supplied to a clock signal generating circuit (not shown) in a controller 30.

In the present modification, by an operation input in the handle 8 to move the end effector 12 (opened or closed between a first grasping piece 1 and a second grasping piece 2) which is necessarily performed during treatment, the gear 52 which is a moving part rotationally moves. The rotational movement of the gear 52 is converted into electric energy. For this reason, in the present modification as well, electric energy to be converted into treatment energy can be supplied to each of the amplifier circuits 27A to 27C for long periods and multiple times during treatment, without increasing labor of the operator, as with the first embodiment.

In the first embodiment and the modification thereof, based on an operation input to move the end effector (12), the moving part (7; 52) rotates relative to the housing (2). The energy converter (40) converts a rotational movement (kinetic energy) of the moving part (7; 52) into electric energy, and the converted electric energy is stored in the electricity storage (21).

Second Embodiment

Next, a second embodiment of the present invention will be explained in reference to FIG. 4. In the second embodiment, the configuration of the first embodiment is modified as follows. Note that the same parts as those in the first embodiment are provided with the same reference numbers, and explanations thereof are omitted.

In the present embodiment, an energy converter 40 includes a piezoelectric element 55 in place of the regeneration motor (41; 50). The piezoelectric element 55 is disposed inside a housing 2 and can be pressed by a portion of a handle 8 inserted into the housing 2. By moving the handle 8 to open or close relative to a grip 6 of the housing 2, a pressing force from the handle 8 to the piezoelectric element 55 varies, and the piezoelectric element 55 expands or contracts. That is, based on an operation input to open or close between a first grasping piece 15 and a second grasping piece 16 (an operation input to move an end effector 12), the handle 8, which is a moving part, moves (performs an advance or retreat movement) relative to the housing 2, thereby the piezoelectric element 55 expands or contracts. In the present embodiment, by closing the handle 8 relative to the grip 6 (arrow X1 in FIG. 4), the piezoelectric element 55 contracts (arrow Y1 in FIG. 4). By opening the handle 8 relative to the grip 6 (arrow X2 in FIG. 4), the piezoelectric element 55 expands (arrow Y2 in FIG. 4).

In the present embodiment, in the energy converter 40, the piezoelectric element 55 expands or contracts by an advance or retreat movement (an opening or closing movement) of the handle 8, by which electric power is generated in the piezoelectric element 55. With this configuration, the advance and retreat movement of the handle 8 is converted into electric energy. That is, the energy converter 40 converts kinetic energy due to the movement of the handle 8, which is a moving part, relative to the housing 2, into electric energy.

Also in the present embodiment, an electric power converter 45 is provided. An energy converter 40 is electrically connected to the electric power converter 45 via electric paths 56A and 56B. Also in the present embodiment, in the energy converter 40 (piezoelectric element 55), kinetic energy is converted into electric energy, thereby generating alternating-current electric power. That is, by the closing movement of the handle 8 relative to the grip 6 (arrow X1 in FIG. 4), the piezoelectric element 55 contracts (arrow Y1 in FIG. 4), thus electric current flows from the piezoelectric element 55 toward the electric path 56A. On the other hand, by the opening movement of the handle 8 relative to the grip 6 (arrow X2 in FIG. 4), the piezoelectric element 55 expands (arrow Y2 in FIG. 4), electric current flows from the piezoelectric element 55 toward an electric path 56B, and the direction of electric current from the piezoelectric element 55 is opposite to the direction in the case where the piezoelectric element 55 shrinks.

Also in the present embodiment, the electric energy converted in the energy converter 40 is converted from alternative-current electric power into direct-current electric power having a voltage storable in an electricity storage 21 by the electric power converter 45. The electric energy from the energy converter 40 is stored in the electricity storage 21 (charge tank 22) and is supplied to each of amplifier circuits 27A to 27C or supplied to a clock signal generating circuit (not shown) in a controller 30.

In the present embodiment, by an operation input in the handle 8 to move the end effector 12 (opening or closing between the first grasping piece 15 and the second grasping piece 16), which is necessarily performed during treatment, the handle 8 which is a moving part performs an advance or retreat movement (an opening or closing movement). Thus, the advance and retreat movement of the handle 8 is converted into electric energy. For this reason, also in the present embodiment, electric energy to be converted into treatment energy can be supplied to each of the amplifier circuits 27A to 27C for long periods and multiple times during treatment, without increasing the labor of the operator, as with the first embodiment.

Modification of Second Embodiment

Note that in a modification of the second embodiment shown in FIG. 5, the energy converter 40 includes a piezoelectric element 61 which is disposed inside a housing 2, and the piezoelectric element 61 can be pressed by operation buttons 35A and 35B. By moving each of operation buttons 35A and 35B to perform an advance or retreat movement, the pressing force from each of the operation buttons 35A, 35B to the piezoelectric element 61 varies, and the piezoelectric element 61 expands or contracts. That is, based on an operation input to supply treatment energy to an end effector 12, each of the operation buttons 35A and 35B, which are moving parts, moves relative to the housing 2 (performs an advance and retreat movement), thereby the piezoelectric element 61 expands or contracts. In the present modification, by pressing each of the operation buttons 35A and 35B (arrow X'1 in FIG. 5), the piezoelectric element 61 contracts (arrow Y'1 in FIG. 5). By releasing the pressing in each of the operation buttons 35A and 35B (arrow X'2 in FIG. 5), the piezoelectric element 61 expands (arrow Y'2 in FIG. 5).

In the present modification, in the energy converter 40, the piezoelectric element 61 expands or shrinks by the advance or retreat movement of each of the operation buttons 35A and 35B, thus electric power is generated in the piezoelectric element 61. With this configuration, the advance and retreat movement of each of the operation buttons 35A and 35B is converted into electric energy. That is, the energy converter 40 converts kinetic energy due to the movement of each of the operation buttons 35A and 35B, which are moving parts relative to the housing 2, into electric energy.

Also in the present modification, in the energy converter 40 (piezoelectric element 61), kinetic energy is converted into electric energy, thereby alternating-current electric power is generated. That is, by causing the piezoelectric element 61 to shrink (arrow Y' 1 in FIG. 5), electric current flows from the piezoelectric element 61 toward an electric path 56A. On the other hand, by causing the piezoelectric element 61 to stretch (arrow Y'2 in FIG. 5), electric current flows from the piezoelectric element 61 toward an electric path 56B, and the direction of electric current from the piezoelectric element 61 is opposite to the direction in the case where the piezoelectric element 61 contracts.

Also in the present modification, the electric energy converted in the energy converter 40 is converted from alternating-current electric power to direct-current electric power having a voltage storable in the electricity storage 21 by an electric power converter 45. In the present modification, however, the battery unit 3 is not provided, and the electricity storage 21 includes a battery 58 in place of the charge tank 22. In the present modification, electric energy from the energy converter 40 is stored in the battery 58 in the electricity storage 21 and is supplied to each of the amplifier circuits 27A to 27C, or supplied to a clock signal generating circuit (not shown) in a controller.

In the present modification, by an operation input to supply treatment energy to the end effector 12, which is necessarily performed during treatment, the operation buttons 35A and 35B, which are moving parts, individually perform an advance and retreat movement. And each advance and retreat movement of the operation buttons 35A and 35B is converted into electric energy. For this reason, also in the present modification, electric energy to be converted into treatment energy can be supplied to each of the amplifier circuits 27A to 27C for long periods and multiple times during treatment, without increasing labor of the surgeon, as with the embodiments explained above.

In the second embodiment and the modification thereof, based on the operation input to move the end effector (12) or the operation input to supply energy to the end effector (12), the moving part (8; 35A, 35B) performs an advance and retreat movement relative to the housing (2). Thus, the energy converter (40) converts the advance and retreat movement (kinetic energy) of the moving part (8; 35A, 35B) into electric energy, and the converted energy is stored in the electricity storage (21).

Other Modification Examples

Note that if the energy converter 40 has the same configuration as each of those of the first embodiment, the modification shown in FIG. 3, and the second embodiment, the energy treatment instrument may have a configuration where an electricity storage 21 includes a battery (58) in place of a charge tank 22, without providing a battery unit 3, as with the modification shown in FIG. 5. Also, if the energy converter 40 has the same configuration as that of the modification shown in FIG. 5, the energy treatment instrument may have a configuration where the battery unit 3 is provided, and the electricity storage 21 includes a charge tank (22) in place of the battery (58), as with each of the first embodiment, the modification shown in FIG. 3 and the second embodiment.

In the embodiments described above, in the end effector 12, a treated target is grasped between the first grasping piece and the second grasping piece; however, the configuration is not limited thereto. For instance, in a certain modification, in an energy treatment instrument (1), a rotation knob (7) and a handle (8) are not provided, and a grip (6) is not provided in a housing (2). In other words, the energy treatment instrument (1) results in a so-called pencil-type energy treatment instrument. In the pencil-type energy treatment instrument (1), an end effector (12) is formed so as to be incapable of grasping a treated target.

However, in the pencil-type energy treatment instrument (1) as well, operation buttons at which the operation to supply treatment energy to the end effector (12) as with the operation buttons (35A, 35B) in the embodiments described above are attached to the housing (2). In the present modification, for instance, an energy converter (40) including the same piezoelectric element as the piezoelectric element (61) in the modification shown in FIG. 5 is disposed inside the housing (2). For this reason, the advance and retreat movement of the operation buttons based on the operation input to supply treatment energy to the end effector (12) is converted into electric energy by the energy converter (40). Electric energy from the energy converter (40) is stored in an electricity storage 21 and is supplied to amplifier circuits (27A to 27C) or a clock signal generating circuit in a controller (30).

That is, also in the present modification of a pencil-type energy treatment instrument (1), operation buttons (35A, 35B), which are moving parts, perform an advance and retreat movement by an operation input to supply treatment energy to the end effector (12), which is necessarily performed during treatment. Thus, the advance and retreat movement of the operation buttons (35A, 35B) is converted into electric energy. For this reason, also in the present modification, electric energy to be converted into treatment energy can be supplied to amplifier circuits (27A to 27C) for long periods. and multiple times during treatment, without increasing the labor of the operator, as with the embodiments explained above.

In the embodiments described above, the energy treatment instrument (1) includes a retainable housing (2), an electricity storage (21) capable of storing electric energy, an end effector (12) configured to perform treatment using treatment energy, and a moving part (7; 8; 35A, 35B; 52) which is disposed so as to be movable relative to the housing (2), and which moves relative to the housing (2) based on an operation input to move the end effector (12) or an operation input to supply treatment energy to the end effector (12). The energy treatment instrument (1) includes an energy converter (40) configured to convert kinetic energy due to a movement of the moving part (7; 8; 35a, 35b; 52) into electric energy, and configured to store the converted electric energy in the electricity storage (21).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An energy treatment instrument comprising:
    a retainable housing;
    an electricity storage capable of storing electric energy;
    an end effector configured to perform treatment using treatment energy;
    a moving part which is disposed so as to be movable relative to the housing, and which is configured to move relative to the housing based on an operation input to move the end effector or an operation input to supply the treatment energy to the end effector; and
    an energy converter configured to convert kinetic energy brought by a movement of the moving part into electric energy, and configured to store the converted electric energy in the electricity storage.

2. The energy treatment instrument according to claim 1, wherein the energy converter is configured to convert a rotational movement of the moving part into the electric energy.

3. The energy treatment instrument according to claim 2, wherein
the moving part includes a rotation knob which is attached to the housing to be rotatable around an axis, and in which an operation to rotate the end effector around the axis is input, and
the energy converter is configured to convert a rotational movement of the rotation knob, based on an operation input to rotate the end effector, into the electric energy.

4. The energy treatment instrument according to claim 1, wherein the energy converter is configured to convert an advance and retreat movement of the moving part into the electric energy.

5. The energy treatment instrument according to claim 4, wherein
the end effector includes a first grasping piece, and a second grasping piece which is openable. and closable relative to the first grasping piece,
the moving part includes a handle which performs an opening and closing movement relative to the housing by an advance and retreat movement, and in which an operation to open or close between the first grasping piece and the second grasping piece is input, and
the energy converter is configured to convert the opening and closing movement of the handle relative to the housing, based on the operation input to open or close between the first grasping piece and the second grasping piece, into the electric energy.

6. The energy treatment instrument according to claim 1, further comprising:
an electric power converter configured to convert alternating-current electric power generated by a change from the kinetic energy to the electric energy in the energy converter to direct-current electric power having a voltage storable in the electricity storage.

7. The energy treatment instrument according to claim 1, wherein the electricity storage includes a charge tank.

8. The energy treatment instrument according to claim 7, wherein the charge tank is a capacitor.

9. The energy treatment instrument according to claim 1, further comprising:
a treatment energy generator configured to generate the treatment energy by being supplied with the electric energy stored in the electricity storage.

* * * * *